United States Patent [19]

Da Silva et al.

[11] Patent Number: 5,368,867
[45] Date of Patent: Nov. 29, 1994

[54] PROCESS FOR THE ACCELERATED PRODUCTION OF STABLE SOLUTIONS, IN EQUILIBRIUM, OF PERACETIC ACID IN LOW CONCENTRATIONS

[75] Inventors: Alcides B. Da Silva; Joao B. Tognetti; Jal R. Dadabhoy, all of Sao Paulo, Brazil

[73] Assignee: Peroxidos Do Brasil, Sao Paolo, Brazil

[21] Appl. No.: 923,978

[22] PCT Filed: Feb. 22, 1991

[86] PCT No.: PCT/BR91/00002
§ 371 Date: Sep. 22, 1992
§ 102(e) Date: Sep. 22, 1992

[87] PCT Pub. No.: WO91/13059
PCT Pub. Date: Sep. 5, 1991

[30] Foreign Application Priority Data

Feb. 23, 1990 [BR] Brazil ............................ PI9000909

[51] Int. Cl.$^5$ ............................................. A01N 31/02
[52] U.S. Cl. ................................ 424/616; 252/186.23; 514/557; 514/607; 562/2; 562/3
[58] Field of Search ................. 424/616; 562/2, 3; 514/557, 607; 423/584; 252/186.23

[56] References Cited

U.S. PATENT DOCUMENTS 4,051,058  9/1977  Bowing et al. ................. 424/616
4,297,298 10/1981  Crommelynck et al. ......... 424/616

FOREIGN PATENT DOCUMENTS 0024219  2/1981  European Pat. Off. .

Primary Examiner—Richard L. Raymond
Assistant Examiner—Scott C. Rand
Attorney, Agent, or Firm—Larson and Taylor

[57] ABSTRACT

The production of dilute equilibrium, storage stable solutions of peracetic acid from mixtures of aqueous hydrogen peroxide and acetic acid, or by dilution of more concentrated peracetic acid solutions, takes a long time because of the low concentrations of the active participating materials. The process can be accelerated by employing a two step procedure in which a concentrated peracetic acid solution is diluted with water and partially hydrolysed in the first step, and then the hydrolysis reaction is quenched by addition of hydrogen peroxide in the second step.

5 Claims, No Drawings

PROCESS FOR THE ACCELERATED PRODUCTION OF STABLE SOLUTIONS, IN EQUILIBRIUM, OF PERACETIC ACID IN LOW CONCENTRATIONS

The present invention relates to the technical field of solutions containing peroxidised products intended for oxidative treatment. More precisely, the invention relates to a process for the production within a short period of time of stable solutions, in equilibrium, based on an organic peroxy acid in low concentrations.

The use of solutions containing peroxidised products as oxidising agents, bleaching agents or microbiocides has been part of the state of the art for some time. These applications are widespread when the products are peroxycarboxylic acids, particularly peracetic acid. When used as biocide, peracetic acid is effective against a wide spectrum of micro-organisms in general, particularly algae, fungi, bacteria and viruses. This biocidal action is due to the strong oxidising power of this product which destroys a large number of components of the cellular membrane thus preventing their chemical/osmotic function and consequently their cellular activity.

Since these microbiocidal properties are well known, the majority of the advances that have occurred in the art relate to improvements either in the formulae of these chemical compounds, aimed at guaranteeing safety of application, stability and effectiveness or in the production process aimed at simplifying the operating technique with a consequent reduction of costs.

It is well known from the state of the art that the use of concentrated solutions of peroxidised products implies the risk of fire, decomposition with liberation of gases, attack on the skin, nasal mucous membranes, etc. It is also known that in a large proportion of the applications in laundries, grape-pressing vats and cooling towers, these products are used in a highly dilute form. However, re-dilution has proved necessary before the product is used by the user, which is undesirable because of the operating risks. Also, this dilution causes a disequilibrium which, as a rule, results in considerable losses of the microbicidal efficiency.

Some patents describe formulations of dilute solutions of peracetic acid, for example, Brazilian patent PI 760 5307 (dated Aug. 13, 1976) describes the preparation of solutions stable in storage with oxidising, bleaching and microbicidal characteristics on the basis of hydrogen peroxide (25.0–40.0% by weight), peracetic acid or perpropionic acid (0.5–20% by weight), stabilisers (up to 1.0% by weight) and surfactants (0.05–5.0% by weight) in which the molar ratio of hydrogen peroxide to peracetic acid and/or acetic acid is between 3.00 and 50.0, i.e. with a molar ratio of peracetic and/or acetic acid to hydrogen peroxide of between 0.02 and 0.33. In accordance with the patent, the disadvantage is avoided of diluting the concentrate which, apart from making the solution unstable during storage, requires strict safety measures during operation. Using phosphonic acids also makes it possible to maintain the stability of the solutions for a relatively long period.

In the same way, patent specification PCT/US87/01147 (dated May 14, 1987) also describes the preparation of stable microbicidal solutions which can be safely transported in boats and which are based on hydrogen peroxide (0.2–8% by weight), peracetic and acetic acid (0.2–11.0% by weight), stabilisers (up to 1.0% by weight) and surfactants (approximately 1.0% by weight) in which the molar ratio of total acid to hydrogen peroxide is between 1.0 and 11.0.

Nevertheless it has been observed that it is perfectly possible to obtain formulations that are safe in transport and application, stable during storage and efficient as regards the microbicidal and oxidising properties.

The main drawback of these processes like that of the others that are part of the state of the art, is the considerable amount of time necessary for the state of equilibrium to be reached in the solutions proposed.

This is due to the fact that the chemical reactions for the formation of organic peroxy acids are equilibrium reactions, which equilibrium is achieved in the diluted solutions over a relatively long period. The reaction for the formation of an organic peroxy acid from the corresponding acid reacting with hydrogen peroxide is represented by the following chemical equation:

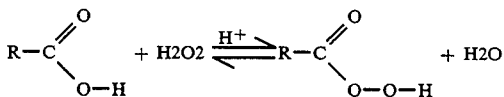

where:
R = aliphatic radial
H+ = mineral, sulphonic or phosphonic acids

For example, for the preparation of a stable solution, in equilibrium, of 30% by weight peracetic acid, only two days are required. The preparation of 2 or 0.2% by weight solutions of peracetic acid requires 16 and 20 days respectively even in the presence of catalysts of the mineral, sulphonic or phosphonic type.

This drawback is mentioned in U.S. Pat. No. 4,297,298 (dated Oct. 27, 1981) as one of the main restrictions for the industrial scale production of peracetic acid solution in low concentrations. A process is proposed for the preparation of dilute stable solutions of an organic peroxide (e.g. peracetic acid) in two stages. In the first stage, the concentrated peracetic acid solution is prepared from the corresponding carboxylic acid or anhydride and concentrated hydrogen peroxide in the presence of small quantities of strong acid as catalyst. In the second stage, this concentrated peracetic acid solution is hydrolysed with a diluent solution containing at least one of the reagents used in the first stage so as to adjust the peracetic acid concentration to the desired level.

This is a process for the production of solutions of organic peroxy acid in low concentrations which, without a doubt, reduces the equilibrium time in comparison with the conventional process. However, the solution proposed by this invention is not complete. At least two factors contribute negatively, making it difficult for a state of equilibrium to be reached within a minimum possible reaction time:

1. The dilution of the concentrated solution with a solution containing at least one of the reagents causing a reduction in the concentration of the acid catalyst and consequently reducing the kinetics of the system;
2. The introduction of at least one of the reagents into the system by the diluent solution causing a reduction in the rate of hydrolysis of the peroxy acid.

Such factors are in fact responsible for the state of equilibrium to be reached in the solutions in not less than 6 days.

The applicant has developed a process which represents the object of the present invention, which makes it possible to considerably reduce the time necessary to reach a constant concentration of peracetic acid in the process for the production of these solutions.

A process is now proposed for the accelerated production of stable solutions, in equilibrium, of peracetic acid in low concentrations in which a concentrated peracetic acid solution is diluted characterised in that concentrated solutions of peracetic acid are used as the starting material preferably containing a low concentration of hydrogen peroxide, according to which the stable solutions, in equilibrium, of peracetic acid in low concentrations are obtained by a controlled hydrolysis of peracetic acid by dilution with water and permitting hydrolysis in the presence of added acidic equilibration catalyst to continue for a period less than that required to attain an equilibrium and in a second step quenching thereof by the addition of hydrogen peroxide.

The main advantage of the process according to the present invention is the considerable reduction in time necessary for obtaining a stable solution, in equilibrium, of organic peroxy acid in low concentrations. As illustrated by examples, holding times of the order of 2 to 5 days are perfectly feasible whereas it is known that the processes according to the state of the art require a considerably longer period to reach the desired equilibrium.

In accordance with the process now proposed, the peracetic acid present in the stable solution, which is in equilibrium from the outset and obtained by conventional processes, is subjected to a hydrolysis reaction controlled by the addition of the necessary quantity of water which may be distilled or demineralised. This hydrolysis reaction is carried out in a tank in the presence of catalysts and preferably stabilisers and wetting surfactants. At the appropriate moment or when the peracetic acid content is in the vicinity of the desired value, this hydrolysis reaction is quenched by the addition of hydrogen peroxide in the quantity anticipated for reaching the new equilibrium conditions for the resulting solutions of peracetic acid in low concentration.

The addition of catalyst during the hydrolysis phase and the introduction of hydrogen peroxide at the moment when the peracetic acid content is near the desired concentration are fundamental for this equilibrium to be reached in the minimum possible reaction time.

Stable solutions, in equilibrium, of peracetic acid in low concentrations are considered to be those which contain between 0.05 and 2.5% by weight peracetic acid; 1.0 and 7.0% by weight hydrogen peroxide; 0.01 and 1.5% by weight, often from 0.2 to 1.5% by weight and sometimes up to 1.0% by weight catalyst; 0.01 and 1.0% by weight stabiliser; 0.05 and 5.0% by weight wetting surfactant and the necessary quantities of water and acetic acid. Stable solutions, in equilibrium, of peracetic acid in high concentrations are considered to be those which contain between 12.0 and 46.0% by weight peracetic acid; 3.0 and 24.0% by weight hydrogen peroxide; 0.01–1.0% by weight catalyst; 0.01–1.0% by weight stabiliser; 0.05–5.0% by weight wetting surfactant and the necessary quantities of water and acetic acid. We consider the mineral, sulphonic or phosphonic acids and the derivatives thereof as suitable catalysts. We consider pyridine carboxylates and derivatives thereof as suitable stabilisers and, finally, alkylaryl sulphonates and the derivatives thereof as suitable wetting surfactants.

The preferred incorporation of the stabilising and wetting agents gives rise to the resulting solutions of peracetic acid in low concentrations which have improved stabilisation during storage and better efficiency as regards the microbicidal and oxidising properties.

Below, examples are given of the practical execution of the objectives of the present application without these limiting the scope of the matter claimed.

The stable starting solution, in equilibrium, of peracetic acid (I) in high concentration is prepared by the addition of 266 kg of an aqueous 68% hydrogen peroxide solution in a reactor containing 727 kg glacial acetic acid, the temperature being controlled and agitation being carried out. Subsequently, the catalyst (7 kg mineral acid) and the stabiliser (0.24 kg pyridine dicarboxylate) are added. The equilibrium is reached after a maximum of 2 days at 25° C. and with an approximate composition of: 313 kg peracetic acid, 40 kg hydrogen peroxide, 480 kg acetic acid, 160 kg water and approximately 7 kg catalyst and stabiliser.

EXAMPLE 1

A stable solution, in equilibrium, of peracetic acid in low concentration is prepared by the addition of 666 kg demineralised water and 10 kg catalyst in a reactor containing 285 kg of (I). The peracetic acid concentration of 2.2% is reached within 4 days at 25° C. Subsequently, 39 kg of a 72.4% aqueous hydrogen peroxide solution are added. The equilibrium is reached immediately and the solution in equilibrium is approximately as follows: 22 kg peracetic acid, 69 kg hydrogen peroxide, 190 kg acetic acid, 709 kg water and approximately 10 kg catalysts.

EXAMPLE 2

A stable solution, in equilibrium, of peracetic acid in low concentration is prepared by the addition of 934 kg demineralised water and 10 kg catalyst in a reactor containing 29 kg of (I). The peracetic acid concentration of 0.13% is reached in 5 days at 25° C. Subsequently, 27 kg of a 72.4% aqueous hydrogen peroxide solution are added. The equilibrium is reached immediately and the solution in equilibrium is approximately as follows: 1.3 kg peracetic acid, 24.1 kg hydrogen peroxide, 20.4 kg acetic acid, 944.2 kg water and approximately 10 kg catalyst.

We claim:

1. A process for the accelerated production of stable solutions, in equilibrium, of peracetic acid in low concentration in which a concentrated peracetic acid solution is diluted, characterised in that the concentrated peracetic acid solution is in a first step diluted with water and permitted to hydrolyse in the presence of an added acidic equilibration catalyst for a period less than that required to attain an equilibrium solution and in a second step the hydrolysis is quenched by addition of hydrogen peroxide to attain a dilute equilibrium peracetic acid solution.

2. A process according to claim 1 characterised in the concentrated peracetic acid solution before dilution contains a low concentration of hydrogen peroxide.

3. A process according to claim 2 characterised in that the concentrated peracetic acid solution before dilution contains between 12.0 and 46.0% by weight peracetic acid.

4. A process according to any preceding claim characterised in that the product solution of the second step contains between 0.05 and 2.5% by weight peracetic acid and between 1.0% and 7.0% by weight hydrogen peroxide.

5. A process according to claim 1, 2, or 3 characterised in that the solution in the first step contains from 0.2 to 1.5% by weight of an acidic equilibration catalyst, from 0.01 to 1.0% by weight of a stabiliser for peroxidic species and from 0.05 to 5.0% by weight of a wetting agent.

* * * * *